United States Patent [19]

Moore

[11] Patent Number: 4,602,029

[45] Date of Patent: Jul. 22, 1986

[54] 1-SUBSTITUTED-3-POLYHALOALKYLTHIO HYDANTOIN FUNGICIDES

[75] Inventor: Joseph E. Moore, Richmond, Calif.

[73] Assignee: Chevron Research Company, San Francisco, Calif.

[21] Appl. No.: 661,003

[22] Filed: Oct. 15, 1984

[51] Int. Cl.⁴ ............... A01N 43/50; C07D 233/82
[52] U.S. Cl. ............................... 514/390; 514/391; 548/311
[58] Field of Search ............ 548/311; 514/389, 391, 514/390

[56] References Cited

U.S. PATENT DOCUMENTS

| | | | |
|---|---|---|---|
| 2,553,770 | 5/1951 | Kittleson | 548/311 X |
| 3,960,883 | 6/1976 | Hubele | 548/311 |
| 4,110,462 | 8/1978 | Takayama et al. | 548/311 X |
| 4,547,517 | 10/1985 | Kühle et al. | 548/311 X |

FOREIGN PATENT DOCUMENTS

| | | | |
|---|---|---|---|
| 3305203 | 8/1984 | Fed. Rep. of Germany | 548/311 |
| 1353558 | 5/1974 | United Kingdom | 548/311 |
| 2127820 | 4/1984 | United Kingdom | 548/311 |

*Primary Examiner*—Richard A. Schwartz
*Attorney, Agent, or Firm*—S. R. LaPaglia; T. G. DeJonghe; S. L. Biggs

[57] ABSTRACT

Compounds of the formula:

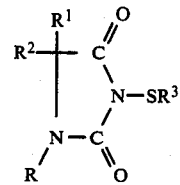

wherein R is aryl of 6 to 12 carbon atoms, substituted aryl substituted with 1 to 3 substituents independently selected from halogen lower alkyl of 1 to 4 carbon atoms, lower alkoxy of 1 to 4 carbon atoms, lower alkylthio of 1 to 4 carbon atoms, nitro, cyano or $S(O)_n R^4$ wherein n is 1 or 2 and $R^4$ is lower alkyl of 1 to 4 carbon atoms; lower alkylamino of 1 to 6 carbon atoms; the group

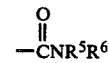

where $R^5$ and $R^6$ are independently hydrogen, lower alkyl of 1 to 6 carbon atoms, aryl or substituted aryl; or alkyl of 1 to 10 carbon atoms, lower cycloalkyl of 3 to 8 carbon atoms, lower alkenyl of 2 to 6 carbon atoms, lower alkynyl of 2 to 6 carbon atoms, alkoxyalkyl of 2 to 8 carbon atoms, or alkylthioalkyl of 2 to 8 carbon atoms, all optionally substituted with 1 to 3 halogen atoms; $R^1$ and $R^2$ are independently hydrogen, or lower alkyl of 1 to 6 carbon atoms; and $R^3$ is lower alkyl of 1 to 3 carbon atoms substituted with 3 to 6 halogen atoms or trihalovinyl, are fungicidal.

20 Claims, No Drawings

1-SUBSTITUTED-3-POLYHALOALKYLTHIO HYDANTOIN FUNGICIDES

BACKGROUND OF THE INVENTION

The present invention relates to certain 1-substituted-3-polyhaloalkyl hydantoins which exhibit fungicidal activity.

Certain 3-polyhaloalkylthio compounds, including substituted hydantoins, have been disclosed as fungicidal. See, e.g., U.S. Pat. Nos. 2,553,770; 2,553,775; 3,178,447; 3,271,245; and 4,012,359.

In addition U.S. Pat. No. 3,860,605 discloses certain N-thiohydantoin compounds as useful as inhibitors of premature vulcanization in rubber.

SUMMARY OF THE INVENTION

The fungicidal compounds of the present invention may be represented by the general formula:

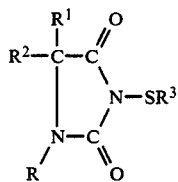

wherein R is aryl of 6 to 12 carbon atoms; substituted aryl substituted with 1 to 3 substituents independently selected from halogen, lower alkyl of 1 to 4 carbon atoms, lower alkoxy of 1 to 4 carbon atoms, lower alkylthio of 1 to 4 carbon atoms, nitro, cyano or the group $-S(O)_nR^4$ where n is 1 or 2 and $R^4$ is lower alkyl of 1 to 4 carbon atoms; lower alkylamino of 1 to 6 carbon atoms; the group

wherein $R^5$ and $R^6$ are independently hydrogen, lower alkyl of 1 to 6 carbon atoms, aryl or substituted aryl; or alkyl of 1 to 10 carbon atoms, cycloalkyl of 3 to 8 carbon atoms, lower alkenyl of 2 to 6 carbon atoms, lower alkynyl of 2 to 6 carbon atoms, alkoxyalkyl of 2 to 8 carbon atoms or alkylthioalkyl of 2 to 8 carbon atoms all each optionally substituted with 1 to 3 independently selected halogen atoms; $R^1$ and $R^2$ are independently hydrogen, or lower alkyl of 1 to 6 carbon atoms; and $R^3$ is lower alkyl of 1 to 3 carbon atoms substituted with 3 to 6 halogen atoms or trihalovinyl.

Among other factors, the present invention is based on my finding that the present compounds are surprisingly effective as fungicides. In particular, these compounds are surprisingly effective in controlling certain fungi which cause plant fungal diseases.

Preferred R groups include aryl, substituted aryl, cycloalkyl and alkoxyalkyl.

Preferred $R^1$ groups include lower alkyl.

Preferred $R^2$ groups include hydrogen.

Preferred $R^3$ groups include those where the halogen substituents are chlorine or chlorine and fluorine, and include, for example, trichloromethyl, 1,1,2,2-tetrachloroethyl, 1,2,2,2-tetrachloroethyl, trichlorovinyl, 2-fluoro-1,1,2,2-tetrachloroethyl, and dichlorofluoromethyl.

Particularly, preferred are compounds wherein one of $R^1$ or $R^2$ is methyl and the other is hydrogen.

Particularly preferred R groups include methoxyethyl, phenyl, and cyclohexyl.

Particularly preferred $R^3$ groups include trichloromethyl.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group $-(CH_2)_m-$ wherein m is an integer greater than zero. Typical alkylene groups include, methylene, ethylene, propylene and the like.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkylthioalkyl" refers to an alkyl group substituted with an alkylthio group. The term "lower alkylthioalkylene" refers to groups having up to a total of 8 carbon atoms and includes, for example, ethylthiomethylene, methylthiomethylene, 2-methylthiopropylene, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkyl" refers to an alkyl group substituted with an alkoxy group. The term "lower alkoxyalkylene" refers to groups having up to a total of 8 carbon atoms and includes, for example, ethoxymethyl, methoxymethyl, 2-methoxypropyl, and the like.

The term "alkenyl" refers to unsaturated alkyl groups having a double bond [e.g., $CH_3CH=CH(CH_2)_2$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo and iodo.

The term "haloalkenyl" refers to alkenyl groups substituted with from 1 to 3 halogen atoms. "Lower haloalkenyl" refers to groups having a total of from 2 to 6 carbon atoms, and includes, for example, 1-chloropropenyl, 2,3-dibromo-but-3-enyl, and the like.

The term "alkynyl" refers to unsaturated alkyl groups having a triple bond (e.g., $CH_3C\equiv CCH_2CH_3$) and includes both straight- and branched-chain alkynyl groups. "Lower alkynyl" refers to groups having a total of from 2 to 6 carbon atoms. Typical lower alkynyl groups include propynyl, but-3-ynyl, hex-4-ynyl, 2-methyl-pent-4-ynyl, and the like.

The term "hydroxy alkyl" refers to the group —R'′-′OH wherein R'′ is branched or unbranched alkylene and the hydroxy can be on a primary, secondary or a tertiary carbon. Examples include hydroxy ethyl and 2-hydroxypropyl and 2-hydroxy-2-methyl butyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, p-methylbenzyl and 2-phenylethyl.

The term "alkylamino" refers to the group R'R'′N- wherein R' is alkyl and R'′ is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "hydantoin" refers to the group

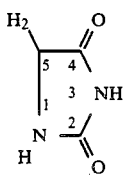

which has the above-noted numbering system.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

DETAILED DESCRIPTION OF THE INVENTION

The compounds of the present invention may be conveniently prepared according to the following reaction scheme:

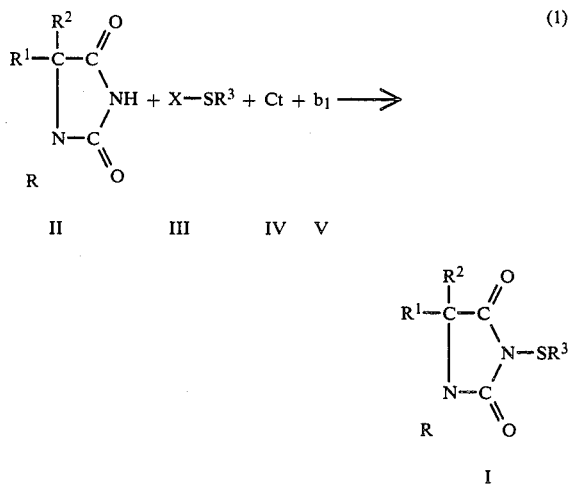

wherein R, $R^1$, $R^2$ and $R^3$ are as previously defined in conjunction with formula (I) and X is halogen, $b_1$ is a base; and Ct is a phase transfer catalyst.

Reaction (1) is conducted by combining II, III, IV and V in solvent. It is preferred to add V to a mixture of II, III and IV in solvent. Preferably, pre-cooled (to about 7° C.) V is added to a cooled mixture of II, III and IV. Although equimolar amounts of II, III and V may be used, it is preferred to use an excess of III and V relative to II, on the order of from about 1.05 to about 1.10 equivalents III per equivalent II, and from about 1.1 to about 1.25 equivalents V per equivalent II. It is preferred to use a catalytic amount of IV (on the order of about 0.02 to about 0.1 equivalent IV per equivalent II). Suitable solvents include organic solvents such as methylene chloride, chloroform, benzene, and the like. Suitable bases $b_1$ include strong inorganic bases such as aqueous sodium hydroxide, or potassium hydroxide, and the like or organic bases, such as pyridine, triethylamine and the like. Suitable phase transfer catalysts include quaternary ammonium and phosphonium salts. One such catalyst is the tricaprylyl methyl ammonium chloride sold under the trademark Aliquat ® 336. Other catalysts include benzyl triethyl ammonium chloride. The reaction is conducted at a temperature of about 4° C. to about 50° C., preferably from about 7° C. to about 35° C., and is generally complete within about 0.1 to about 1 hour. The product, I, is isolated by conventional procedures such as extraction, washing, stripping, filtration, crystallization, chromatography, and the like.

Some starting materials, II, are commercially available. Other starting materials II may be conveniently prepared from commercially available materials by methods well known to those skilled in the art. See, e.g., Examples 2, 3, 5 to 7 and 9 to 11.

UTILITY

The compounds of the present invention are useful in controlling a wide variety of pests.

These compounds are active as fungicides and are particularly effective in controlling a variety of fungi which are deleterious to plants, including plant fungal infections. Some of these compounds are useful in controlling leaf blights caused by organisms such as *Phytophthora infestans, Septoria apii, Alternaria solani conidia,* and powdery mildews such as that caused by *Erisiphe polygoni.* However, some of the compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 1-Methyl-3-(trichloromethylthio)hydantoin

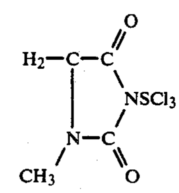

A mixture of 11.4 g (0.1 mole) 1-methylhydantoin, 1.2 g Aliquat® 336 and 19.5 g (0.1 mole) trichloromethylsulfenyl chloride in 100 ml methylene chloride was stirred vigorously and cooled in an ice bath. To that mixture, 25 g of 20% pre-cooled aqueous sodium hydroxide was added at once; the temperature of the reaction mixture increased from 5° C. to 21° C. Stirring was continued; the ice bath was removed after 5 minutes. The methylene chloride layer was washed with water, dried over magnesium sulfate and stripped to give 24 g of sticky solids. Crystallization from toluene with charcoal treatment gave 8.4 g of the above-identified product, as a white solid, melting point 110°-112° C.

Elemental analysis for $C_5H_5Cl_3N_2O_2S$ showed: calculated %C 22.70, %H 1.91, and %N 10.62; found %C 23.77, %H 1.97, and %N 11.61.

EXAMPLE 2

Preparation of N-[(1-cyano-1-methyl)ethyl]-N-ethyl urea

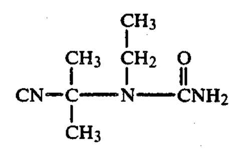

A mixture of 11.2 g (0.1 mole) 2-(ethylamino)-2-methylpropionitrile, 16.2 g (0.2 mole) potassium cyanate, 12 g (0.2 mole) acetic acid and 75 ml ethanol was stirred at reflux for 1.0 hour. The reaction mixture was filtered hot to remove insolubles. The reaction mixture was allowed to cool; solids separated which were isolated by filtration and dried to give the above identified product as a white solid, melting point 210°-268° C.

A small amount was recrystallized from ethanol to give a white solid, melting point 288°-308° C.

Elemental analysis for $C_7H_{13}N_3O_7$ showed: calculated %C 54.03, %H 8.36, and %N 26.99; found %C 53.99, %H 8.32, and %N 27.65.

EXAMPLE 3

Preparation of 1-Ethyl-5,5-dimethylhydantoin

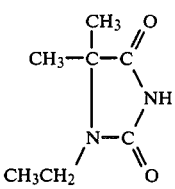

A mixture of 29.9 g (0.19 moles) N-[(1-cyano-1-methyl)-ethyl]-N-ethyl urea (the product of Example 2) and 60 g (0.33 moles) 20% hydrochloric acid was stirred to give a clear solution and then stirred at gentle reflux for one hour. The clear solution was cooled with an ice bath. Solids separated and were filtered and dried to give 13.8 g of white solid. (About 90% liquefied in the range of 120°–130° C., 10% stayed solid above 300° C.) An additional 2.6 g of solid were obtained from the mother liquor.

EXAMPLE 4

Preparation of 1-Ethyl-3-trichloromethylthio-5,5-dimethylhydantoin

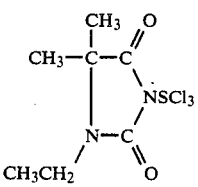

A mixture of 15.6 g (0.1 mole) 1-ethyl-5,5-dimethylhydantoin (the product of Example 3), 19.5 g (0.1 moles) trichloromethylsulfenyl chloride and 1.2 g Aliquat® 336 in 100 ml methylene chloride was stirred vigorously for about 10 minutes. The reaction mixture was cooled to about 7° C. in an ice bath; 25 g (0.125 moles) of pre-cooled 20% aqueous sodium hydroxide were added at once. After the addition, the temperature of the reaction mixture rose to 27° C.; when the temperature returned to about 7° C., the ice bath was removed. The reaction mixture was washed three times with 50 ml ice water, dried over magnesium sulfate and stripped to give a solid. The solid was crystallized twice from toluene with charcoal treatment to give 16.0 g of the above-identified product as a white solid, melting point 141°–142° C.

Elemental analysis for $C_8H_{11}Cl_3N_2O_2S$ showed: calculated %C 31.44, %H 3.63, and %N 9.16; found %C 31.52, %H 3.68, and %N 9.32.

EXAMPLE 5

Preparation of N-(2-Propionitrile)-N-phenylcarbamoyl chloride

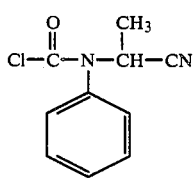

Phosgene, 23.0 g (0.23 mole) was absorbed in 300 ml methylene chloride. To that stirred solution, a solution of 29.2 g (0.2 mole) 2-(phenylamino)-propionitrile and 15.8 g (0.2 mole) pyridine in 50 ml methylene chloride was dropped in over 30 minutes. Stirring was continued for 5 minutes. The reaction mixture was washed twice with 100 ml ice water and once with 100 ml ice water containing 20 ml concentrated hydrochloric acid, dried over magnesium sulfate and stripped to give 41 g of a brown oil which soon solidified. The solids were washed with about 100 ml hexane, filtered and dried to get 39.7 g of the above-identified product as a brown solid, melting point 76° to 80° C.

EXAMPLE 6

Preparation of 2[(N-carbamoyl-N-phenyl)-amino]propionitrile

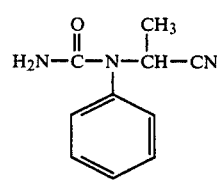

Into a stirred mixture of 39.7 g N-(2-propionitrile)-N-phenylcarbamoyl chloride (the product of Example 5) in 250 ml methylene chloride, ammonia gas was bubbled over a period of 2 hours 15 minutes with evolution of heat and precipitation of solids. The solids were filtered and dried to give 29.9 g of white solid; melting at 170° C. with a trace of solids melting at 210° C. The filtrate was stripped to give 13.9 g of light brown solid melting at 170° C. The solids were combined to give a yield of 43.8 g of the above-identified product.

EXAMPLE 7

Preparation of 1-Phenyl-5-methylhydantoin

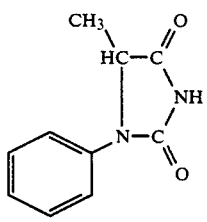

A mixture of 43.8 g 2-[(N-carbamoyl-N-phenyl)-amino]propionitrile (the product of Example 6) in 200 ml 20% hydrochloric acid was heated at reflux for 15 minutes. The reaction mixture was cooled to about 25° C., filtered and the solids were washed well with water. The solids were dissolved in methylene chloride, dried over magnesium sulfate, and stripped to give 30.5 g of product as a beige solid, melting point 149°–150° C.

Recrystallization of 1.0 g of product from toluene with carbon treatment gave 0.7 g of white solid, melting point 149°–150° C.

Elemental analysis for $C_{10}H_{10}N_2O_2$ showed: calculated %C 63.14, %H 5.30, and %N 14.72; found %C 62.33, %H 5.57, and %N 14.27.

EXAMPLE 8

Preparation of
1-Phenyl-3-trichloromethylthio-5-methylhydantoin

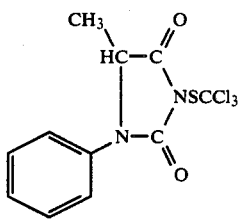

A stirred mixture of 8.0 g (0.042 mole) 1-phenyl-5-methylhydantoin, 8.6 g (0.046 mole) trichloromethylsulfenyl chloride and 1.0 g Aliquat® 336 in 100 ml methylene chloride was cooled in an ice bath. To that mixture a pre-cooled sodium hydroxide solution (4.2 g of 50% sodium hydroxide diluted to 20 g with water) was added at once. The temperature of the reaction mixture rose from 3° C. to 5° C.; stirring was continued for 10 minutes. The methylene chloride layer was separated and washed well with water, dried over magnesium sulfate and stripped to give 15.5 g of an oil. After being washed with cold hexane, the oil slowly solidified. The solid was crystallized from hexane-toluene to give 9.9 g of the above-identified product as a white solid, melting point 113°–114° C.

Elemental analysis for $C_{11}H_9Cl_3N_2O_2S$ showed: calculated %C 38.39, %H 2.67, and %N 8.24; found %C 40.44, %H 2.79, and %N 8.25.

EXAMPLE 9

Preparation of 2-(Methoxyethylamino)-propionitrile

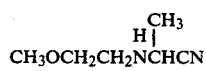

To a stirred solution of 62.4 g (0.6 mole) sodium bisulfite in 200 ml water which had been cooled in an ice bath, 26.5 g (0.6 mole) acetaldehyde were added over 5 minutes. The ice bath was removed. The reaction mixture was stirred 2.5 hours; then 45 g (0.6 mole) 2-methoxyethylamine were added (with evolution of heat). The reaction mixture was stirred 2 hours; then 39 g (0.6 mole) potassium cyanide were added with heat evolution and the resulting mixture was stirred at ambient temperature. After about 30 minutes, a second phase separated; the reaction mixture was stirred 3 hours and then allowed to stand overnight. The reaction mixture was extracted with 150 ml methylene chloride. The methylene chloride extract was dried over magnesium sulfate and stripped to give 67.4 g of the light yellow oil. The oil was distilled under vacuum to give 60.6 g of the above-identified product as a clear, colorless oil, boiling at 60° C. at 0.20 mm.

EXAMPLE 10

Preparation of
2-[(N-Chlorocarbonyl-N-methoxyethyl)amino]propionitrile

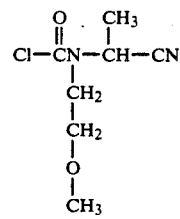

To a stirred mixture of 19.9 g (0.2 mole) phosgene and 300 ml methylene chloride cooled in an ice bath, a mixture of 25.68 g (0.2 mole) 2-(methoxyethylamino)propionitrile (the product of Example 9) and 15.8 g (0.2 mole) pyridine in 50 ml methylene chloride were dropped in over about 40 minutes. The ice bath was removed and stirring was continued for 15 minutes. The reaction mixture was washed twice with 100 ml ice water and once with 100 ml ice water containing 20 ml concentrated hydrochloric acid, dried over magnesium sulfate and stripped to give 35.9 g of the above-identified product, as a yellow oil.

EXAMPLE 11

Preparation of
2-[(N-Carbamoyl-N-methoxyethyl)amino]propionitrile

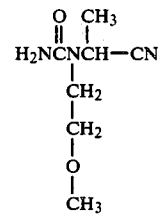

Into a stirred mixture of 35.4 g 2-[(N-chlorocarbonyl-N-methoxyethyl)amino]propionitrile (the product of Example 10) in 200 ml methylene chloride, ammonia gas was bubbled for about 2 hours. The exothermicity of the addition kept the temperature of the reaction mixture at about 36° C. for about 75 minutes. Solids (ammonium chloride salt) were removed by filtration. The solvent was stripped to give 31.8 g of the above-identified product as a yellow oil.

EXAMPLE 12

Preparation of 1-Methoxyethyl-5-methylhydantoin

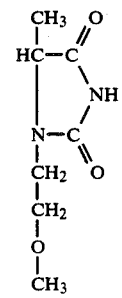

A mixture of 31.8 g 2-[(N-carbamoyl-N-methoxyethyl)amino]propionitrile (the product of Example 11) and 63.6 g of 20% hydrochloric acid were stirred at gentle reflux for one hour. The aqueous acid was removed by stripping. The residue was taken up in 150 ml methylene chloride, dried over magnesium sulfate and stripped to give 23.8 g of crude product as a viscous yellow oil.

An 8.0 g portion of the oil was chromatographed on 165 g of silica gel, eluting with 2% methanol to give 5.9 g of colorless oil which quickly solidified, melting point 52°-65° C. The solid was crystallized from hexane/toluene to give a white solid, melting point 64°-67° C.

Elemental analysis for $C_7H_{12}N_2O_3$ showed: calculated %C 48.83, %H 7.02, and %N 16.26; found %C 48.21, %H 6.98 and %N 16.39.

EXAMPLE 13

Preparation of
1-Methoxyethyl-3-trichloromethylthio-5-methylhydantoin

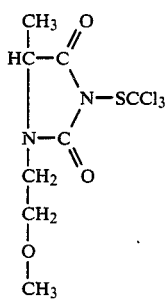

A stirred mixture of 8.6 g (0.05 mole) 1-methoxyethyl-5-methylhydantoin (the product of Example 12), 10.2 g (0.055 mole) trichloromethylsulfenyl chloride and 1.0 g Aliquat ® 336 in 100 ml methylene chloride was cooled in an ice bath. To that mixture a precooled sodium hydroxide solution (5.0 g of 50% sodium hydroxide diluted to 25 g) was added at once. After the addition, the temperature of the reaction mixture increased from 5° to 15° C. After 5 minutes the ice bath was removed; stirring was continued for about 25 minutes. The aqueous phase was separated. The organic phase was dried and stripped to give an oil. The oil was washed with hexane to give 14.1 g of a semi-solid. The semi-solid was taken up in 50 ml chloroform and applied to a column of 225 g silica gel; elution with 2% methanol in chloroform gave 10.1 g of the above-identified product as a viscous orange oil.

Elemental analysis for $C_8H_{11}Cl_3N_2O_3S$ showed: calculated %C 29.87, %H 3.45, and %N 8.70; found %C 30.53, %H 3.73, and %N 8.71.

Compounds made in accordance with Examples 1 to 13 are found in Table I.

EXAMPLE A

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum*, *Rhizoctonia solani*, *Fusarium moniloforme*, *Botrytis cinerea*, *Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of $mg/cm^2$ needed for 99½ control of the fungus ($ED_{99}$). The effectiveness of the compounds for fungicidal activity are reported in Table II in terms of the percent of the $ED_{99}$ of the test compound of the $ED_{99}$ of the standard Difolatan ®.

EXAMPLE B

Grape Downy Mildew

Compounds were tested for the control of the Grape Downy Mildew organism, *Plasmopara viticola*. Seedlings of *Vitis vinifera* var. Emperor (7+ weeks old) were used as hosts. The plants were sprayed with a 200 ppm solution of the test compound in an acetone and water solution containing a small amount of nonionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

EXAMPLE C

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humdity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE D

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE E

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with actone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table II.

EXAMPLE G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table II.

EXAMPLE H

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table II.

TABLE I

Compounds of the formula:

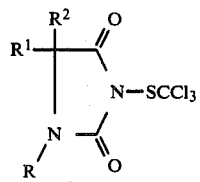

| | | | | | Elemental Analysis | | | | | |
|---|---|---|---|---|---|---|---|---|---|---|
| | | | | Physical | % C | | % H | | % N | |
| Compound | R | R¹ | R² | State | Calc. | Found | Calc. | Found | Calc. | Found |
| 1 41837 | —CH₃ | —H | —H | white solid, mp 110–112° C. | 22.78 | 23.77 | 1.91 | 1.97 | 10.62 | 11.61 |
| 2 41196 | —CH₃ | —CH₃ | —CH₃ | white solid, mp 123–124° C. | 28.84 | 29.16 | 3.11 | 3.11 | 9.61 | 10.37 |
| 3 41562 | —CH₂CH₃ | —CH₃ | —H | yellow oil | 28.84 | 28.71 | 3.11 | 3.19 | 9.61 | 9.73 |
| 4 41197 | —CH₂CH₃ | —CH₃ | —CH₃ | white solid, mp 141–142° C. | 31.14 | 31.52 | 3.63 | 3.68 | 9.16 | 9.32 |
| 5 41563 | —CH₂CH₂CH₃ | —CH₃ | —H | red oil | 33.81 | 31.86 | 4.10 | 3.98 | 8.76 | 8.47 |
| 6 41614 | —CH(CH₃)₂ | —CH₃ | —H | white solid, | 31.44 | 31.71 | 3.63 | 3.12 | 9.16 | 9.06 |

TABLE I-continued

Compounds of the formula:

$$R^1 - \underset{\underset{\underset{R'}{N}}{|}}{\overset{\overset{R^2}{|}}{C}} \overset{O}{\underset{\underset{O}{\|}}{\overset{\|}{C}}} N-SCCl_3$$

| Compound | R | R¹ | R² | Physical State | %C Calc. | %C Found | %H Calc. | %H Found | %N Calc. | %N Found |
|---|---|---|---|---|---|---|---|---|---|---|
| 7 41790 | —C(CH₃)₃ | —CH₃ | —H | mp 76–77° C. beige solid, mp 69–70° C. | 33.81 | 35.72 | 4.10 | 4.55 | 8.76 | 8.18 |
| 8 41791 | —⟨S⟩ | —CH₃ | —H | beige solid, mp 101–102° C. | 38.12 | 38.82 | 4.37 | 4.48 | 8.1 | 7.76 |
| 9 41498 | —CH₂CH=CH₂ | —CH₃ | —H | beige solid, mp 44–49° C. | 31.64 | 32.52 | 2.99 | 3.19 | 9.22 | 9.05 |
| 10 41705 | —CH₂CH₂OCH₃ | —CH₃ | —H | yellow oil | 29.87 | 30.53 | 3.45 | 3.73 | 8.70 | 8.71 |
| 11 41654 | —N(CH₃)₂ | —CH₃ | —H | white solid, mp 93–94° C. | 27.42 | 28.03 | 3.92 | 3.34 | 13.70 | 13.86 |
| 12 41889 | —⟨phenyl⟩ | —CH₃ | —H | white solid, mp 113–114° C. | 38.39 | 40.44 | 2.67 | 2.79 | 8.24 | 8.25 |
| 13 41890 | —⟨2,4-diCl-phenyl⟩ | —CH₃ | —H | white solid, mp 133–135° C. | 32.33 | 33.88 | 1.73 | 2.0 | 6.85 | 7.43 |
| 14 41423 | —C(O)NHCH₃ | —H | —H | white solid, mp 140–152° C. | 23.50 | 24.29 | 1.97 | 2.15 | 13.69 | 14.68 |
| 15 41424 | —C(O)NH—⟨phenyl⟩ | —H | —H | white solid | 35.83 | 36.64 | 2.19 | 2.12 | 11.39 | 11.58 |

TABLE II

FUNGICIDAL ACTIVITY

| | Mycelial Inhibition | | | | | | | | | | |
|---|---|---|---|---|---|---|---|---|---|---|---|
| Compound | Pyth. | Rhiz. | Fusar. | Botry. | Asper. | GDM | TLB | RB | TEB | CLB | BPM | BR |
| 1 41837 | 0 | 0 | — | 0 | — | — | 14 | 10 | 60 | 29 | 0 | 14 |
| 2 41196 | 56 | 71 | 0 | 33 | 0 | 0 | 0 | 0 | — | 0 | 0 | 0 |
| 3 41562 | 54 | 65 | 100 | 223 | 100 | 58 | 0 | 0 | 33 | 29 | 0 | 0 |
| 4 41197 | 73 | 0 | 0 | 43 | 120 | 14 | 20 | 50 | — | 0 | 0 | 0 |
| 5 41563 | 34 | 75 | 100 | 233 | 130 | 0 | 0 | 20 | 83 | 0 | 0 | 0 |
| 6 41614 | 23 | 95 | — | 100 | 54 | 50 | 8 | 0 | 67 | 0 | 0 | 0 |
| 7 41790 | 0 | 40 | 0 | 36 | 0 | — | 14 | 0 | 67 | 55 | 0 | 0 |
| 8 41791 | — | 38 | 0 | 27 | 0 | — | 100 | 88 | 67 | 82 | 97 | 0 |
| 9 41498 | 0 | 271 | — | 144 | — | 53 | 21 | 0 | 0 | 0 | 29 | 0 |
| 10 41705 | 83 | 100 | 67 | 36 | 111 | 100 | 63 | 0 | 75 | 0 | 0 | 0 |
| 11 41654 | 86 | 133 | — | 286 | 110 | 14 | 0 | 0 | — | 0 | 0 | 0 |
| 12 41889 | 100 | 114 | 100 | 100 | 159 | 73 | 87 | 90 | — | 96 | 100 | 8 |
| 13 41890 | 83 | 100 | 100 | 100 | 82 | 80 | 80 | 80 | — | 78 | 96 | 0 |
| 14 41423 | 28 | 76 | — | 49 | — | 0 | 0 | 0 | 0 | 0 | 0 | 0 |
| 15 41424 | 20 | 83 | 0 | 80 | — | 62 | 43 | 0 | 0 | 25 | 0 | 0 |

Pyth. = *Pythium ultimum*
Rhiz. = *Rhizoctonia solani*
Fusar. = *Fusarium moniloforme*
Botry. = *Botrytis cineria*
Asper. = *Aspergillus niger*
TLB = Tomato Late Blight
RB = Rice Blast
TEB = Tomato Early Blight
CLB = Celery Late Blight
BPM = Bean Powdery Mildew
BR = Bean Rust
— = not tested or test failed

What is claimed is:

1. A compound of the formula:

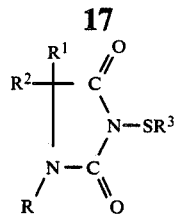

wherein R is alkoxyalkyl of 2 to 8 carbon atoms, $R^1$ and $R^2$ are independently hydrogen or lower alkyl of 1 to 6 carbon atoms; and $R^3$ is lower alkyl of 1 to 3 carbon atoms substituted with 3 to 6 halogen atoms or trihalovinyl.

2. A compound according to claim 1 wherein $R^1$ is lower alkyl.

3. A compound according to claim 2 wherein $R^2$ is hydrogen.

4. A compound according to claim 3 wherein $R^3$ is trichloromethyl.

5. A compound according to claim 4 wherein $R^1$ is methyl.

6. A compound according to claim 5 wherein R is methoxyethyl.

7. A compound according to claim 1 wherein $R^3$ is trichloromethyl, 1,1,2,2-tetrachloroethyl, trichlorovinyl, 1,2,2,2-tetrachloroethyl, 2-fluoro-1,1,2,2-tetrachloroethyl or dichlorofluoromethyl.

8. A compound according to claim 1 wherein $R^3$ is trichloromethyl.

9. A fungicidal composition which comprises an inert carrier and a fungicidally effective amount of a compound of claim 1.

10. A fungicidal composition which comprises an inert carrier and a fungicidally effective amount of a compound of claim 3.

11. A fungicidal composition which comprises an inert carrier and a fungicidally effective amount of a compound of claim 6.

12. A fungicidal composition which comprises an inert carrier and a fungicidally effective amount of a compound of claim 5.

13. A fungicidal composition which comprises an inert carrier and a fungicidally effective amount of a compound of claim 7.

14. A fungicidal composition which comprises an inert carrier and a fungicidally effective amount of a compound of claim 8.

15. A method of controlling fungi which comprises contacting said fungi or their growth environment with a fungicidally effective amount of a compound of claim 1.

16. A method of controlling fungi which comprises contacting said fungi or their growth environment with a fungicidally effective amount of a compound of claim 3.

17. A method of controlling fungi which comprises contacting said fungi or their growth environment with a fungicidally effective amount of a compound of claim 6.

18. A method of controlling fungi which comprises contacting said fungi or their growth environment with a fungicidally effective amount of a compound of claim 5.

19. A method of controlling fungi which comprises contacting said fungi or their growth environment with a fungicidally effective amount of a compound of claim 10.

20. A method of controlling fungi which comprises contacting said fungi or their growth environment with a fungicidally effective amount of a compound of claim 8.

* * * * *